(12) United States Patent
Kawai

(10) Patent No.: US 8,357,273 B2
(45) Date of Patent: Jan. 22, 2013

(54) ANALYZER

(75) Inventor: Takuji Kawai, Kyoto (JP)

(73) Assignee: Arkray, Inc., Kyoto (JP)

( * ) Notice: Subject to any disclaimer, the term of this patent is extended or adjusted under 35 U.S.C. 154(b) by 1234 days.

(21) Appl. No.: 11/547,945

(22) PCT Filed: Apr. 8, 2005

(86) PCT No.: PCT/JP2005/006918
§ 371 (c)(1),
(2), (4) Date: Oct. 6, 2006

(87) PCT Pub. No.: WO2005/100968
PCT Pub. Date: Oct. 27, 2005

(65) Prior Publication Data
US 2007/0229085 A1    Oct. 4, 2007

(30) Foreign Application Priority Data

Apr. 12, 2004  (JP) ................................. 2004-117123

(51) Int. Cl.
*G01N 33/487* (2006.01)

(52) U.S. Cl. ......... 204/403.01; 204/403.02; 204/403.03; 204/403.04; 204/403.11; 205/775.5; 205/778

(58) Field of Classification Search .......... 204/403.01–403.15; 205/775.5–778
See application file for complete search history.

(56) References Cited

U.S. PATENT DOCUMENTS

| | | | |
|---|---|---|---|
| 5,320,732 A | 6/1994 | Nankai et al. | |
| 5,421,189 A | 6/1995 | Dussault | |
| 5,502,396 A * | 3/1996 | Desarzens et al. | 204/403.02 |
| 6,531,040 B2 | 3/2003 | Musho et al. | |
| 7,491,303 B2 | 2/2009 | Sakata et al. | |
| 2005/0178663 A1 * | 8/2005 | Kobayashi | 204/403.01 |

FOREIGN PATENT DOCUMENTS

| | | |
|---|---|---|
| JP | 4-357449 | 12/1992 |
| JP | 9-508205 | 8/1997 |
| JP | 2000-19147 | 1/2000 |
| JP | 2001-66279 | 3/2001 |
| JP | 2001-356108 | 12/2001 |
| JP | 2002-156358 | 5/2002 |
| JP | 2003-156459 | 5/2003 |
| WO | WO 03/29804 | 4/2003 |
| WO | WO03/076918 A1 * | 9/2003 |

* cited by examiner

*Primary Examiner* — Keith Hendricks
*Assistant Examiner* — Bach Dinh
(74) *Attorney, Agent, or Firm* — Fox Rothschild LLP

(57) ABSTRACT

The present invention relates to an analyzer (1) to be used with an analytical tool (2) mounted thereto and used for analyzing a particular component contained in a sample supplied to the analytical tool (2). The analyzer (1) includes at least one detection terminal pair (11, 12) including a first and a second detection terminals (11A, 11B, 12A, 12B) which are capable of selecting a mutually contacting state and a non-contacting state, a detector (15) for detecting the state of contact of the first and the second detection terminals (11A, 11B, 12A, 12B), and an abnormality detector (16) for detecting an abnormality of the at least one detection terminal pair (11, 12) based on the detection result by the detector (15).

9 Claims, 10 Drawing Sheets

Pattern 3

Pattern 4

Pattern 1

Pattern 2

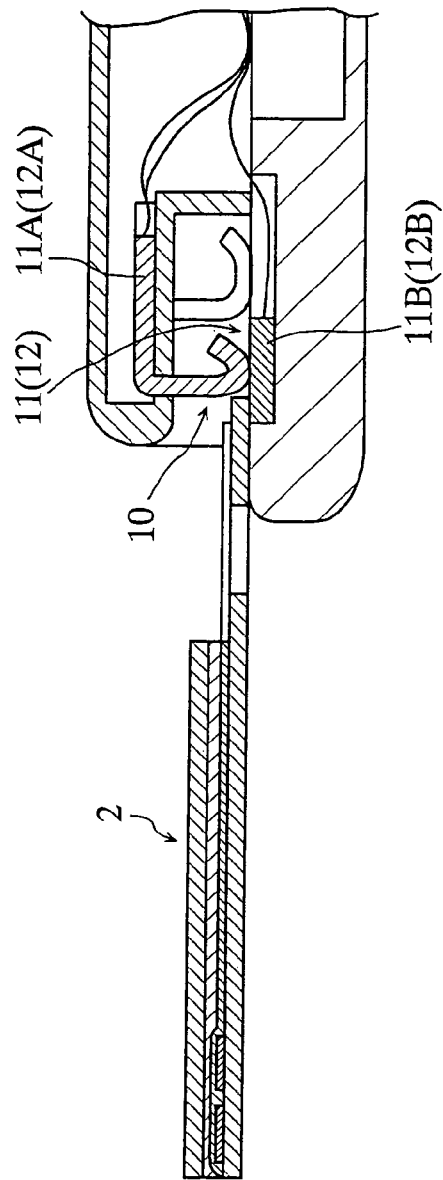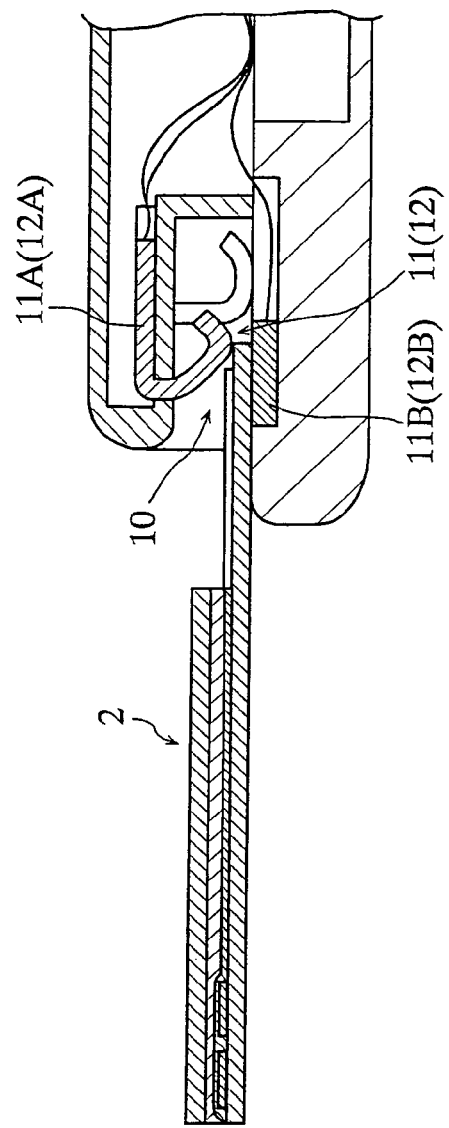

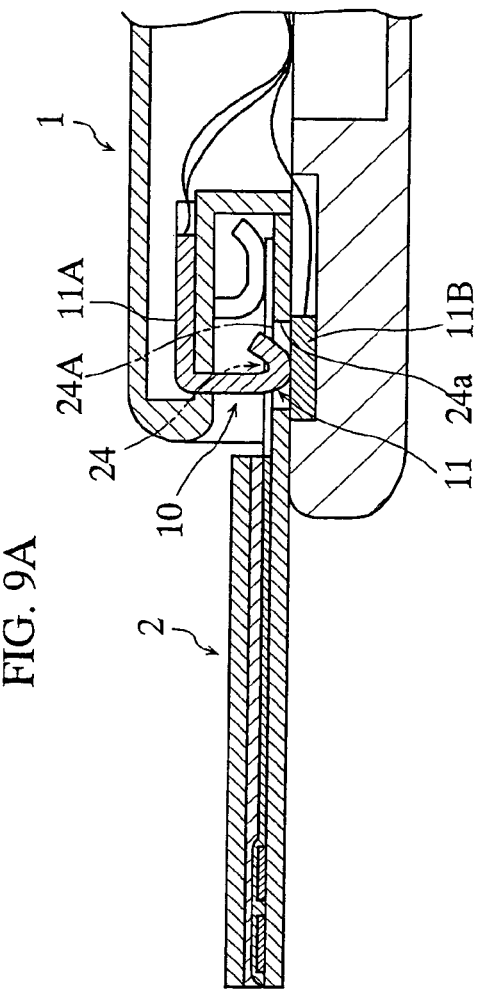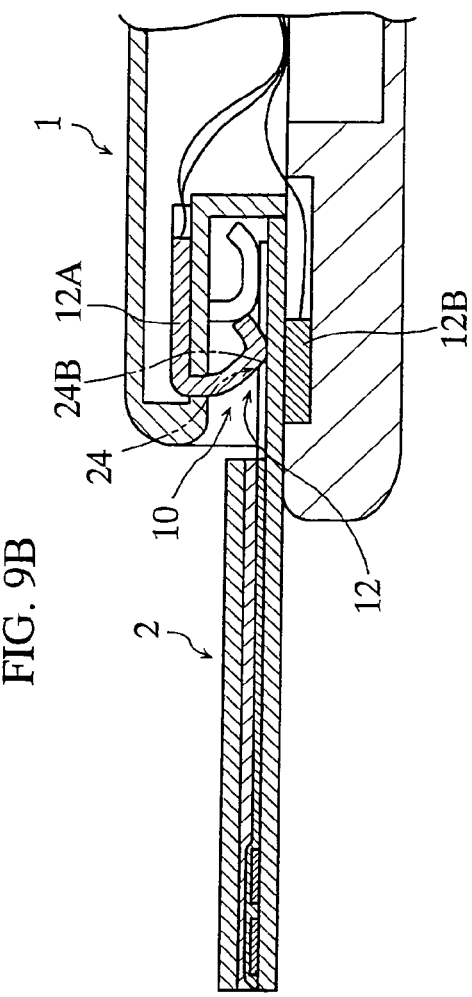

FIG. 10

| | Pattern 1 | Pattern 2 | Pattern 3 | Pattern 4 |
|---|---|---|---|---|
| Through-hole (1st/2nd Detection Region) | Formed/Formed | Formed/None | None/Formed | None/None |
| Signal Combination | Low/Low | Low/High | High/Low | High/High |
| Calibration Curve No. | 1 | 2 | 3 | 4 | ions # ANALYZER

TECHNICAL FIELD

The present invention relates to an analyzer which is used with an analytical tool mounted thereto and used for analyzing a particular component (e.g. glucose or cholesterol) contained in a sample (e.g. blood or urine).

BACKGROUND ART

To measure a blood glucose level, a method is employed which uses a blood glucose level measurer and a biosensor in combination (See Patent Document 1, for example). As the biosensor, use may be made of one having the structure shown in FIGS. 3-6. The illustrated biosensor 2 is designed to measure the blood glucose level by an electrochemical technique and includes a capillary 23 and electrodes 25 and 26. In the capillary 23, a reagent portion 28 is provided. When blood is introduced into the capillary, the capillary provides a reaction field for reaction between the blood and a reagent contained in the reagent portion 28. The electrodes 25 and 26 are utilized for applying a voltage to the reaction field and measuring the response current obtained by the voltage application.

The sensitivity of the biosensor 2 may vary according to the manufacturing factory or the manufacturing line. Therefore, in a blood glucose level measurer, a plurality of calibration curves are stored in advance, and the calibration curve suitable for the sensitivity of the biosensor is selected. The blood glucose level is computed based on the selected calibration curve and the response current. The selection of the calibration curve may be performed manually by the user. As an alternative method, the selection of the calibration curve corresponding to the sensitivity of the biosensor 2 may be performed by making the blood glucose level measurer detect the existence or absence of a through-hole 24a at a recognition target portion 24 of the biosensor 2. Specifically, as will be understood from FIGS. 9A and 9B, detection terminal pairs 11 and 12 in the form of a leaf spring are provided in the blood glucose level measurer 1, and the existence or absence of the through-hole 24a is recognized by detecting whether or not the terminals 11A, 11B, 12A, 12B of the detection terminal pairs 11, 12 are in contact with each other when the biosensor 2 is mounted to the blood glucose level measurer 1.

In normal conditions, when the biosensor 2 is not mounted to the blood glucose level measurer 1, the terminals 11A and 11B (12A and 12B) of the detection terminal pair 11, 12 are in contact with each other. However, one terminal 11A, 12A of the detection terminal pair 11, 12 is in the form of a leaf spring, and its elasticity is reduced due to the repetitive use. Therefore, the terminals 11A and 11B (12A and 12B) may not come into contact with each other although the biosensor 2 is not mounted to the blood glucose level measurer 1. In such a case, as shown in FIG. 11 for example, the terminals 11A and 11B (12A and 12B) of the detection terminal pair 11 (12) do not come into contact with each other even when the through-hole 24a is formed at the recognition target portion 24. When this situation occurs, the blood glucose level measurer 1 determines that the through-hole 24a is not formed at the recognition target portion 24a and selects a wrong calibration curve. As a result, the blood glucose level obtained by the blood glucose level measurer 1 deviates from the correct value.

Patent Document 1: JP-B-H08-10208

DISCLOSURE OF THE INVENTION

An object of the present invention is to avoid erroneous measurement caused by an abnormality of a detection terminal used for recognizing information applied to an analytical tool.

According to the present invention, there is provided an analyzer to be used with an analytical tool mounted thereto and used for analyzing a particular component contained in a sample supplied to the analytical tool. The analyzer comprises at least one detection terminal pair including a first detection terminal and a second detection terminal which are capable of selecting a mutually contacting state and a non-contacting state, a detector for detecting the state of contact of the first detection terminal and the second detection terminal, and an abnormality detector for detecting an abnormality of the at least one detection terminal pair based on detection result by the detector.

For instance in normal conditions, the first and the second detection terminals are in contact with each other when the analytical tool is not mounted and separate from each other in the process of mounting the analytical tool.

In this case, in the process of mounting the analytical tool, for example, the abnormality detector determines that there is no abnormality in the detection terminal pair when shifting of the first and the second detection terminals from the mutually contacting state to the non-contacting state is confirmed and determines that there is an abnormality in the detection terminal pair when shifting of the first and the second detection terminals from the mutually contacting state to the non-contacting state is not confirmed.

The detector may detect the state of contact of the first detection terminal and the second detection terminal after converting an analog electrical signal obtained by utilizing the first and the second detection terminals into a digital electrical signal. Preferably, in this case, the abnormality detector determines that there is no abnormality in the detection terminal pair when the level of the digital electrical signal is higher than a predetermined threshold and determines that there is an abnormality in the detection terminal pair when the level of the digital electrical signal is lower than the predetermined threshold.

Preferably, at least one of the first and the second detection terminals is in the form of a leaf spring.

For instance, the analyzer of the present invention uses an analytical tool provided with a recognition target portion which includes at least one predetermined detection target region and to which intended information is applied by selecting whether or not a through-hole is to be formed at the detection target region. In this case, for example, the first and the second detection terminals are located at a position corresponding to the detection target region when the analytical tool is mounted and utilized for recognizing information applied to the recognition target portion.

For instance, as the analytical tool, the analyzer to which the present invention is applicable uses an analytical tool in which information as to the analytical tool is applied to the recognition target portion, an electrochemical sensor, or an analytical tool configured to analyze a particular component contained in blood.

Preferably, the analyzer of the present invention further comprises a controller for withholding analysis of the particular component in the sample when the abnormality detector determines that there is an abnormality in the detection terminal pair.

BRIEF DESCRIPTION OF THE DRAWINGS

FIG. 8 includes sectional views of a principal portion in the process of mounting the biosensor to the mount portion.

FIG. 9 includes sectional views of a principal portion in a state in which the biosensor is mounted to the mount portion.

FIG. 10 is a table showing formation patterns of a through-hole in a recognition target portion of a biosensor and examples of combination of signals generated by a detector.

BEST MODE FOR CARRYING OUT THE INVENTION

Figure 1:
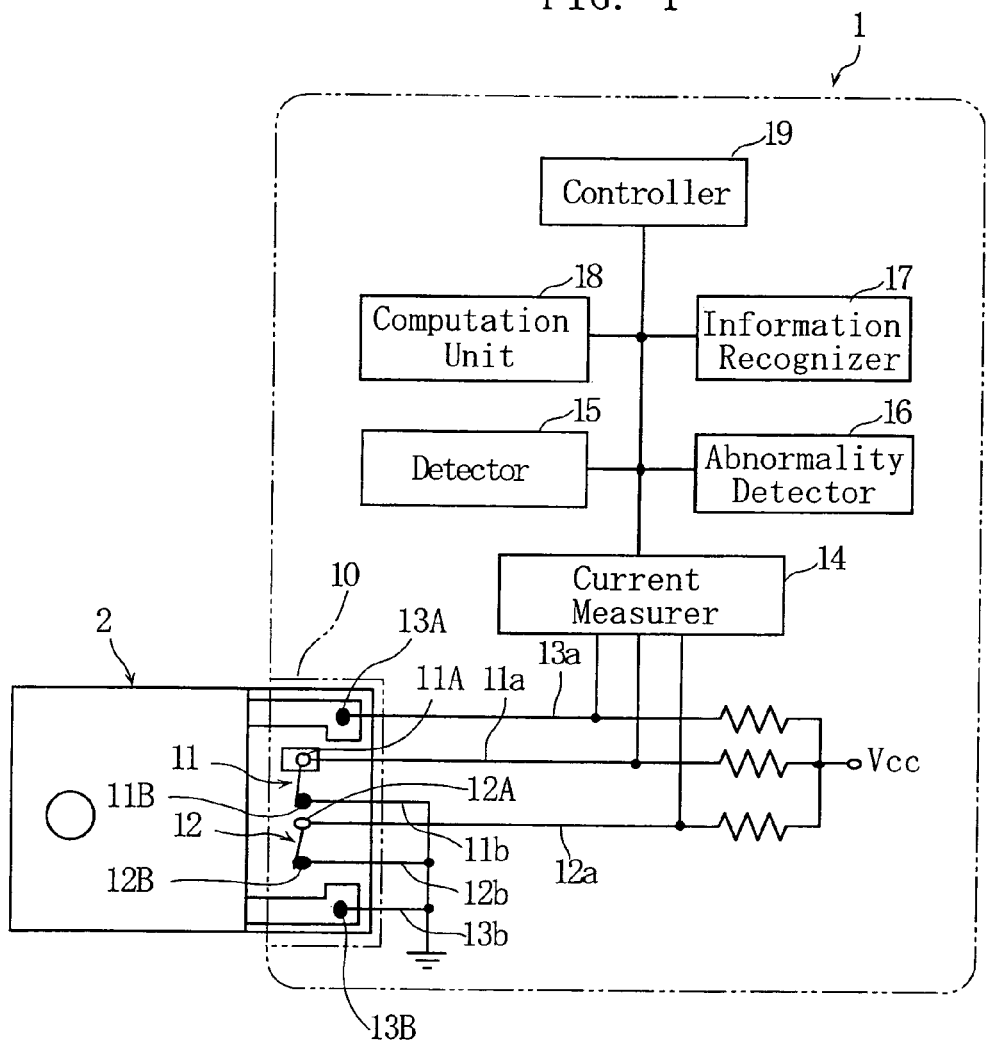
FIG. 1 shows the state in which a biosensor is mounted to a blood glucose level measurer according to the present invention, and the analyzer is shown as a schematic structural view including blocks, whereas the biosensor is shown as a plan view.
Figure 2:
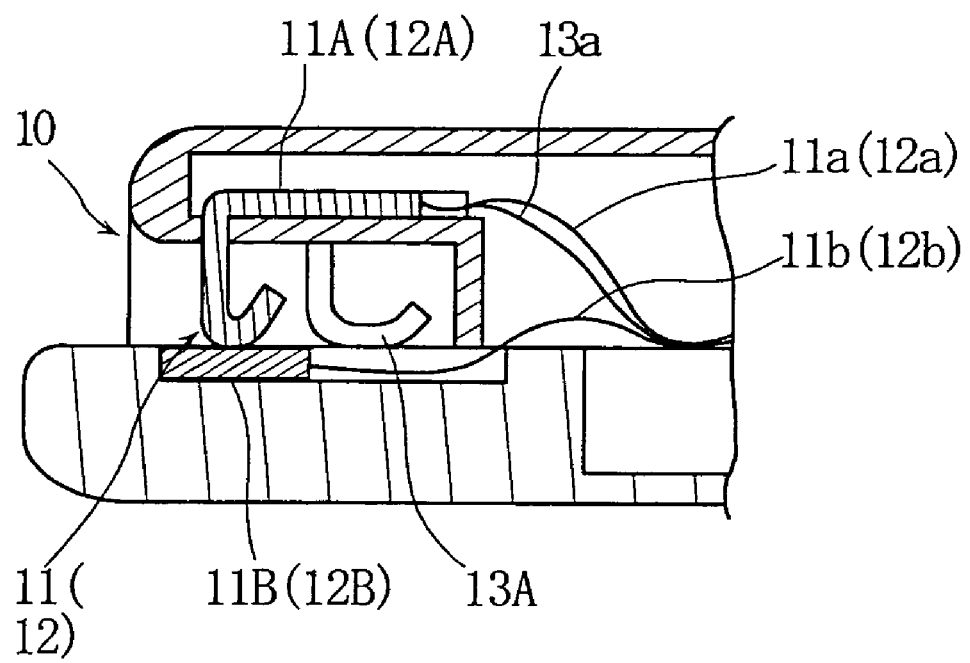
FIG. 2 is a sectional view of a principal portion around a mount portion of the blood glucose level measurer shown in FIG. 1.

FIGS. 1 and 2 show a blood glucose level measurer 1 which is used with a biosensor 2 as an analytical tool mounted thereto for measuring the glucose level in blood (blood glucose level) supplied to the biosensor 2. The blood glucose level measurer 1 includes a mount portion 10, a first and a second pairs 11, 12 of detection terminals, a first and a second measurement terminals 13A and 13B, a power source Vcc, a current measurer 14, a detector 15, an abnormality detector 16, an information recognizer 17, a computation unit 18, and a controller 19.

Figure 3:
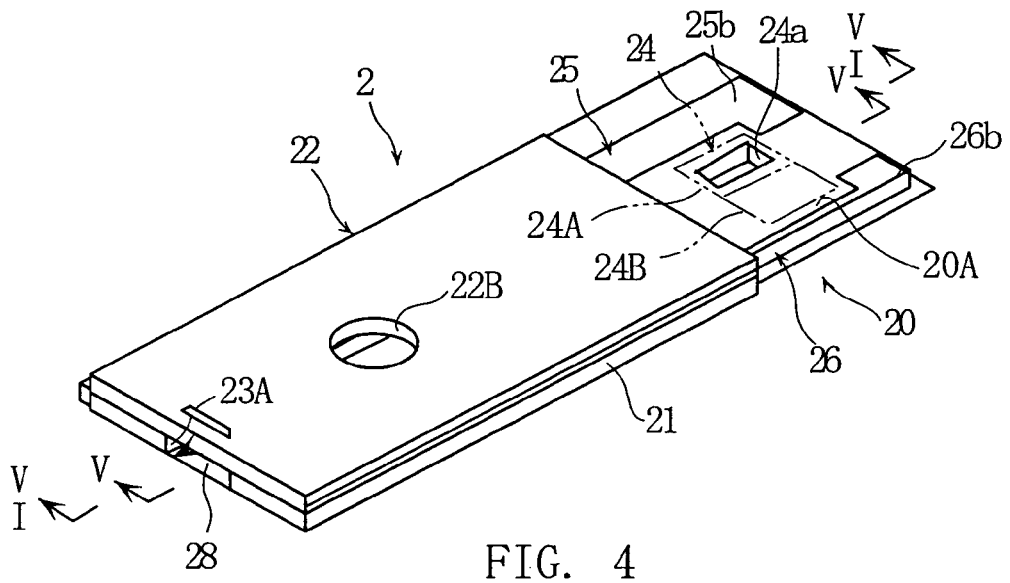
FIG. 3 is an overall perspective view showing the biosensor which is mounted to the blood glucose level measurer in FIG. 1.
Figure 4:
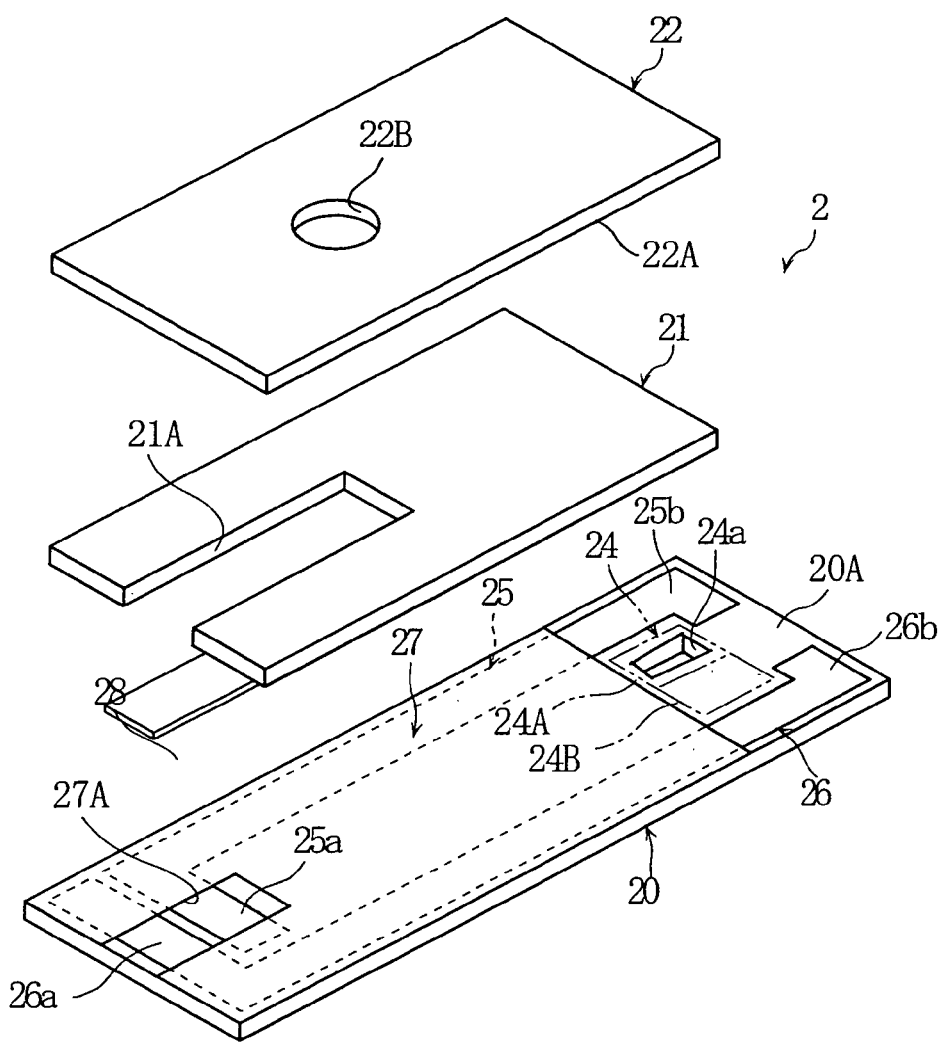
FIG. 4 is an exploded perspective view of the biosensor shown in FIG. 3.
Figure 5:
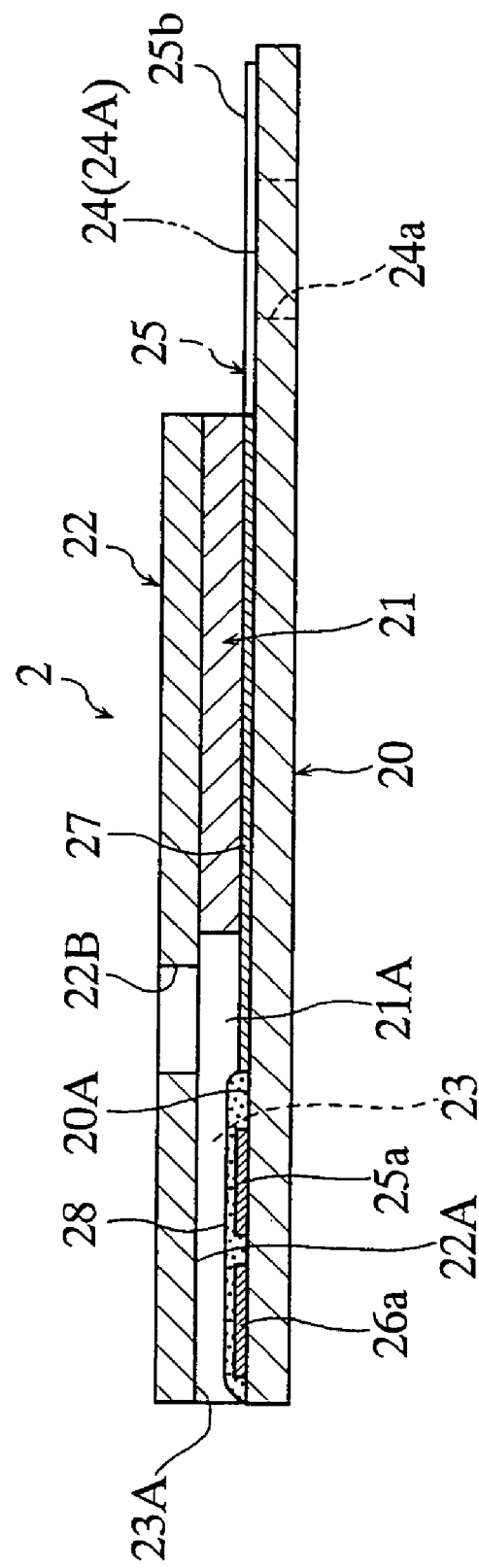
FIG. 5 is a sectional view taken along lines V-V in FIG. 3.
Figure 6:
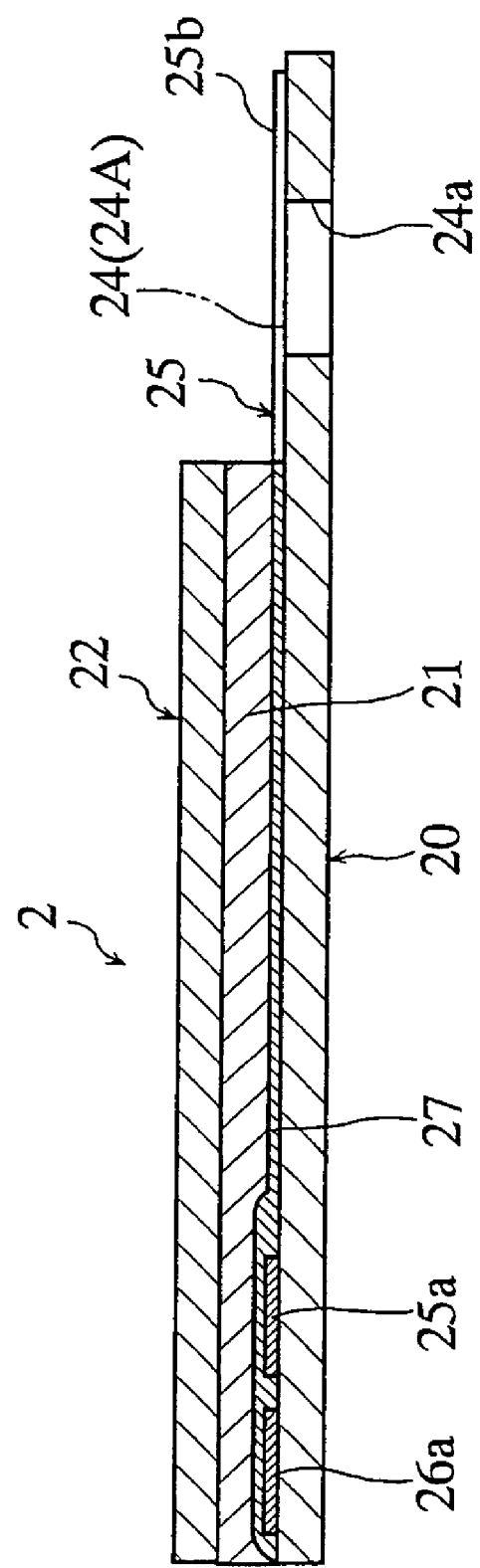
FIG. 6 is a sectional view taken along lines VI-VI in FIG. 3.
Figure 7C:
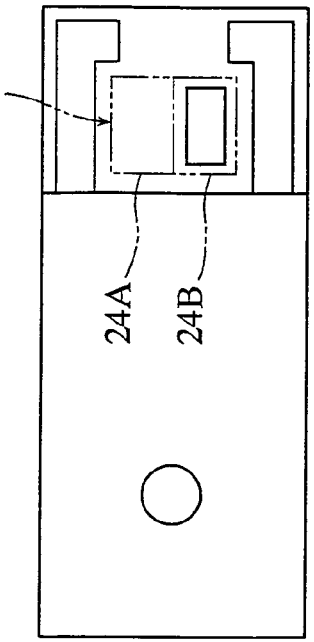
FIG. 7 includes plan views each showing an example of formation of a through-hole in a recognition target portion of the biosensor shown in FIG. 3.
Figure 7D:
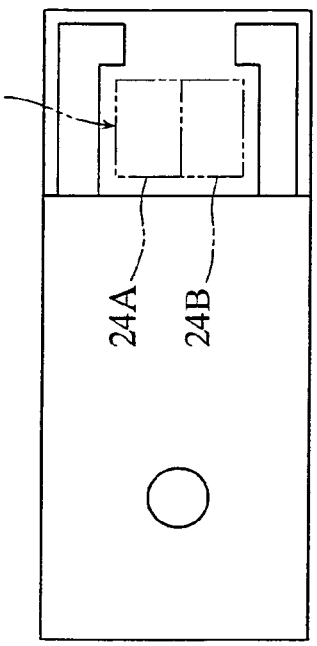
Figure 7A:
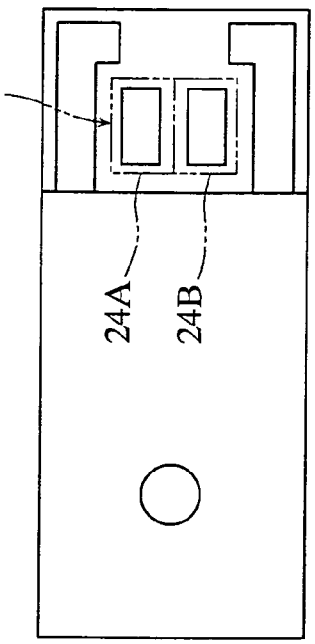
Figure 7B:
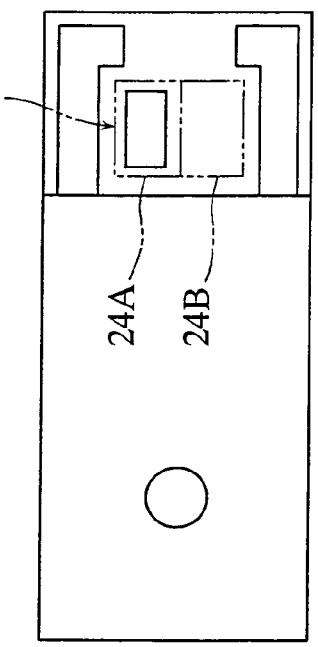

As shown in FIGS. 3 and 6, the biosensor 2 to be mounted to the blood glucose level measurer 1 (See FIGS. 1 and 2) may be disposable, for example, and is designed to measure the blood glucose level. The biosensor 2 comprises a substrate 20 having an elongated rectangular configuration and a cover 22 stacked on the substrate via a spacer 21. In the biosensor 2, a capillary 23 extending longitudinally of the substrate 20 is defined by the elements 20-22.

The spacer 21 serves to define the distance from the upper surface 20A of the substrate 20 to the lower surface 22A of the cover 22, i.e., the height of the capillary 23, and may comprise a double-sided tape. The spacer 21 is formed with a slit 21A having an open end. The slit 21A defines the width of the capillary 23, and the open end of the slit 21A serves as an introduction port 23A for introducing blood into the capillary 23.

The cover 22 includes an exhaust port 22B for discharging air in the capillary 23 to the outside. The cover 22 may be made of a thermoplastic resin having a high wettability such as vinylon or highly crystalline PVA.

The substrate 20 is made of an insulating resin such as PET, for example, and has an elongated rectangular configuration larger tan the cover 22. The substrate 20 includes a portion projecting on a side of the cover 22, and a recognition target portion 24 is provided at this portion. The recognition target portion 24 is a portion through which information on the biosensor 2 can be recognized when the biosensor 2 is mounted to the blood glucose level measurer 1. The recognition target portion includes a first and a second detection target regions 24A and 24B. The first detection target region 24A is provided at a position where the first pair of detection terminals 11 is located when the biosensor 2 is mounted to the blood glucose level measurer 1. The second detection target region 24B is provided at a position where the second pair of detection terminals 12 is located when the biosensor 2 is mounted to the blood glucose level measurer 1. To the recognition target portion 24, intended information is applied by selecting whether or not a through-hole 24a (24b) is formed at each of the detection target regions 24A and 24B. Examples of information to be applied to the recognition target portion 24 include the kind of calibration curve to be used in the computation which will be described later, the manufacture country, the manufacture factory, the lot number, the use-by date and the measurement item (such as whether the component to be measured is glucose or cholesterol). FIGS. 3-6 show the example in which a through-hole 24a is formed at the first detection target region 24A, whereas a through-hole is not formed at the second detection target region 24B. However, as shown in FIGS. 7A-7D, when the recognition target portion 24 includes two detection target regions 24A and 24B, there are four possible combinations of the first and the second detection target regions 24A and 24B with or without through-holes 24a, 24b. Therefore, the intended information selected from four kinds of information can be applied to the biosensor 2. The number of detection target regions of the recognition target portion 24 is not limited to two and may be one or not less than three. However, in the blood glucose level measurer 1, the number of pairs of detection terminals needs to be changed in accordance with the number of detection target regions.

As shown in FIGS. 3-6, the upper surface 20A of the substrate 20 is formed with a working electrode 25, a counter electrode 26, an insulating film 27 and a reagent portion 28. Each of the working electrode 25 and the counter electrode 26 is L-shaped as a whole. Specifically, the working electrode 25 and the counter electrode 26 mostly extend in the longitudinal direction of the substrate 20 and respectively include ends 25 and 26a extending in the width direction of the substrate 1. The working electrode 25 and the counter electrode 26 further include ends 25b and 26b, respectively, which are brought into contact with the first and the second measurement terminals 13A and 13B (See FIGS. 1 and 2) of the blood glucose level measurer 1 when the biosensor 2 is mounted to the blood glucose level measurer 1. The working electrode 25 and the counter electrode 26 can be formed simultaneously by screen printing using conductive carbon ink.

The insulating film 27 covers most part of the working electrode 25 and the counter electrode 26 while exposing the ends 25a, 25b, 26a and 26b of the working electrode 25 and the counter electrode 26. The insulating film 27 is formed with an opening 27A for exposing the ends 25a and 26a of the working electrode 25 and the counter electrode 26. The opening 27A also serves to define the region for forming the reagent portion 28 and has a rectangular configuration extending longitudinally of the substrate 20.

The reagent portion 28 is provided in the capillary 23 so as to bridge the ends 25a and 26a of the working electrode 25 and the counter electrode 26 within the opening 27A of the insulating film 27. For instance, the reagent portion 28 includes an electron mediator and an oxidoreductase and is in the form of a porous solid easily soluble in blood.

For instance, as the oxidoreductase, glucose oxidase (GOD) or glucose dehydrogenase (GDH) may be used, and typically, PQQGDH may be used. For instance, as the electron mediator, ruthenium complex or iron complex may be used, and typically, $[Ru(NH_3)_6]Cl_3$ or $K_3[Fe(CN)_6]$ may be used.

The capillary 23 serves to move the blood introduced through the introduction port 23A in the longitudinal direction of the substrate 20 by utilizing capillary action and retain the introduced blood. Specifically, when blood is introduced through the introduction port 23A, blood moves in the capillary 23 while the air in the capillary 23 is discharged through the exhaust port 22B. In the capillary 23, the reagent portion 28 is dissolved, and a liquid phase reaction system including an electron mediator, an oxidoreductase and glucose is established. The movement of the blood in the capillary 23 stops when the blood reaches an edge of the exhaust port 22B.

The mount portion 10 of the blood glucose level measurer 1 shown in FIGS. 1 and 2 is a portion for holding the biosensor 2. The first and the second pairs 11, 12 of detection terminals and the first and the second measurement terminals 13A, 13B are fixed to the mount portion 10.

The first and the second pairs 11, 12 of detection terminals are utilized for detecting whether or not the recognition target portion 24 of the biosensor 2 is formed with a through-hole 24a (24b). Each pair 11, 12 of the detection terminals includes a terminal 11A, 12A in the form of a leaf spring and a terminal 11B, 12B in the form of a plate. The leaf spring terminals 11A and 12A are held in contact with the plate terminals 11B and 12B, respectively, when the biosensor 2 is not mounted to the mount portion 10 and separate from the plate terminals 11B and 12B when an upward force exceeding a predetermined level is exerted thereto. The leaf spring terminals 11A and 12A are connected to the power source Vcc and the current measurer 14 via wirings 11a and 12a. The plate terminals 11B and 12B are connected to ground via wirings 11b and 12b. Referring to FIG. 9A which exemplarily shows the first detection terminal pair 11, when the first detection target region 24A of the recognition target portion 24 is formed with a through-hole 24a, the leaf spring terminal 11A and the plate terminal 11B are held in a contact state (ON state). Referring to FIG. 9B which exemplarily shows the second detection terminal pair 12, when the second detection target region 24B of the recognition target portion 24 is not formed with a through-hole, the leaf spring terminal 12A and the plate terminal 12B are held in a non-contact state (OFF state).

The first and the second measurement terminals 13A and 13B are utilized for generating a potential difference between the working electrode 25 and the counter electrode 26 of the biosensor 2 and for measuring the current generated at that time. Each of the measurement terminals 13A and 13B comprises a leaf spring and exerts a downward force to the biosensor 2 to hold the biosensor 2 at the mount portion 10 when the biosensor 2 is mounted to the mount portion 10. The first measurement terminal 13A is so arranged as to come into contact with the end 25b of the working electrode 25 when the biosensor 2 is mounted to the mount portion 10. The first measurement terminal 13A is connected to the power source Vcc and the current measurer 14 via a wiring 13a. The second measurement terminal 13B is so arranged as to come into contact with the end 26b of the counter electrode 26 when the biosensor 2 is mounted to the mount portion 10. The second measurement terminal 13B is connected to ground via a wiring 13b.

The power source Vcc shown in FIG. 1 serves to generate a potential difference between the leaf spring terminal 11A, 12A and the plate terminal 11B, 12B of each of the detection terminal pairs 11, 12 or between the first and the second measurement terminals 13A and 13B. As the power source Vcc, a DC power source such as a dry battery may be used.

The current measurer 14 measures whether or not current flows between the leaf spring terminal 11A, 12A and the plate terminal 11B, 12B of each of the detection terminal pairs 11 and 12 in the process of mounting the biosensor 2 to the mount portion 10 or measure, as the current, the amount of electrons supplied from the liquid phase reaction system to the working electrode 25 of the biosensor 2 after the biosensor 2 is mounted to the mount portion 10. The current measurer 14 may include an A/D converter.

The detector 15 detects individually whether or not each of the detection terminal pairs 11 and 12 is in the contact state. Specifically, based on the measurements by the current measurer 14, the detector 15 detects whether or not current flows between the leaf spring terminal 11A, 12A and the plate terminal 11B, 12B of each of detection terminal pair 11 and 12, thereby detecting whether or not the detection terminal pair 11, 12 is in the contact state. When the detection terminal pair 11, 12 is in the contact state, the detector 15 generates a Low signal because current flows between the leaf spring terminal 11A, 11B and the plate terminal 11B, 12B. When the leaf spring terminal 11A, 12A and the plate terminal 11B, 12B are in the non-contact state, the detector 15 generates a High signal, because current does not flow between the terminals 11B, 12B.

Specifically, as shown in FIGS. 8A and 8B, in the process of mounting the biosensor 2 to the mount portion 10, the leaf spring terminal 11A (12A) and the plate terminal 11B (12B) of each detection terminal pair 11 (12) shift from the contact state (ON state) to the non-contact state (OFF state) Therefore, in the detector 15 shown in FIG. 1, a Low signal is first generated and then a High signal is generated in the process of mounting the biosensor 2 to the mount portion 10. After the biosensor 2 is mounted to the mount portion 10, the following signals are generated in the detector 15 in the case where the biosensor 2 to be used has the structure shown in FIGS. 3-6. Specifically, since the through-hole 24a is formed at the first detection target region 24A of the recognition target portion 24, the leaf spring terminal 11A and the plate terminal 11B of the first detection terminal pair 11 become the contact state, as shown in FIG. 9A. Therefore, as the signal corresponding to the first detection terminal pair 11, the detector 15 (See FIG. 1) generates a Low signal. On the other hand, since a through-hole is not formed at the second detection target region 24B of the recognition target portion 24 in the biosensor 2, the leaf spring terminal 12A and the plate terminal 12B of the second detection terminal pair 12 are held in the non-contact state, as shown in FIG. 9B. Therefore, as the signal corresponding to the second detection terminal pair 12, the detector 15 (See FIG. 1) generates a High signal.

When the current measurer 14 includes an A/D converter, the detector 15 can distinguish the magnitude of the current when current flows between the leaf spring terminal 11A, 12A and the plate terminal 11B, 12B. Therefore, the detector 15 may be so designed that, when current flows between the leaf spring terminal 11A, 12A and the plate terminal 11B, 12B, a Low signal is generated if the current is smaller than a predetermined value and a High signal is generated if the current is greater than the predetermined value.

With this structure, when the current flowing between the terminals 11A (12A) and 11B (12B) is reduced due to the deterioration of condition of contact between the leaf spring terminal 11A, 12A and the plate terminal 11B, 12B, i.e., the terminals 11A (12A) and 11B (12B) are in an imperfect contact state or dust and the like exists between the terminals 11A (12A) and 11B (12B) although the terminals are not in the completely non-contact state, such a situation can be detected as an abnormality.

Figure 11:
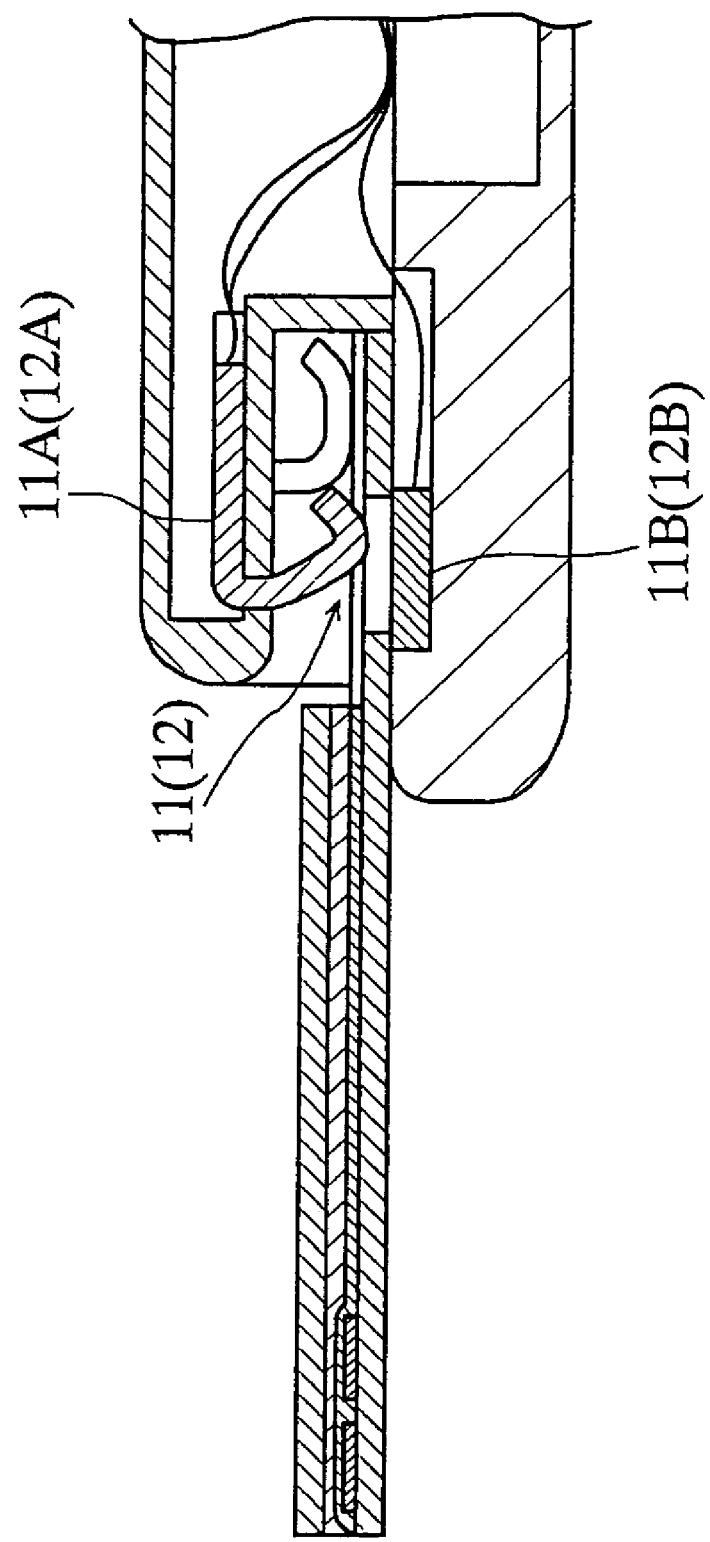
FIG. 11 is a sectional view of a region around a contact portion, showing the state of contact failure of a detection terminal pair of a blood glucose level measurer.

The abnormality detector 16 shown in FIG. 1 detects whether or not there is an abnormality in the first and the second detection terminal pairs 11, 12, i.e., whether or not such a contact failure as shown in FIG. 11 occurs between the leaf spring terminal 11A (12A) and the plate terminal 11B (12B) of the first (second) detection terminal pair 11 (12). Specifically, the abnormality detector 16 is designed to check whether or not there is an abnormality in each of the detection terminal pairs 11 and 12 based on the detection results obtained by the detector 15 in the process of mounting the biosensor 2 to the mount portion 10. As noted before, in the process of mounting the biosensor 2 to the mount portion 10, each of the detection terminal pairs 11 and 12 shifts from the ON state to the OFF state as long as the detection terminal pair is in the normal condition. Therefore, the abnormality detector 16 determines that each of the detection terminal pairs 11 and 12 is normal when it is confirmed that the signal from the detector 15 is shifted from a Low signal to a High signal and otherwise determines that there is an abnormality in the detection terminal pair 11, 12 (e.g. when a Low signal is not detected, a High signal is not detected, or shifting from a High signal to a Low signal occurs).

The information recognizer 17 serves to recognize information applied to the recognition target portion 24 of the biosensor 24. The information recognizer 17 is designed to recognize information applied to the recognition target portion 24 based on the combination of signals obtained via the first and the second detection terminal pairs 11, 12 after the biosensor 2 is mounted to the mount portion 10. For instance, in the biosensor 2 shown in FIGS. 3-6, the first detection target region 24A of the recognition target portion 24 is formed with the through-hole 24a, whereas the second detection target region 24B is not formed with a through-hole, so that the first detection terminal pair 11 is held in the contact state, whereas the second detection terminal pair 12 is held in the non-contact state. Therefore, in the detector 15, a combination of a Low signal and a High signal is generated.

As noted before, when the recognition target portion 24 of the biosensor 2 includes two detection target regions 24A and 24B, there are four possible combinations of the first and the second detection target regions 24A and 24B with or without through-holes 24a, 24b, as shown in FIGS. 7A-7D. Accordingly, as shown in FIG. 10, when the biosensor 2 shown in FIGS. 3-6 is used, there are four possible patterns of combination of a Low signal and a High signal to be generated at the detector 15 and recognized at the information recognizer 17. Therefore, the information recognizer 17 checks the combination of signals (Low signal or High signal) generated by the detector 15 with the biosensor 2 mounted to the mount portion 10, determines which one of the stored patterns the combination of the generated signals correspond to and recognizes, from the four kinds of information, the intended information based on the determination results. For instance, in the case where information as to the calibration curve to be used at the computation unit 18, which will be described later, is applied to the recognition target portion 24 of the biosensor 2, the information recognizer 17 can recognize the intended one from four calibration curves. By changing the program to be stored in advance, the information recognizer can be designed to recognize information other than the kind of calibration curve, such as the manufacture country, the manufacture factory, the lot number and the use-by date of the biosensor 2.

The computation unit 18 performs computation necessary for determining the particular component in the sample supplied to the biosensor 2, based on the current measured at the current measurer 14. For instance, when the information recognizer 17 is designed to recognize the calibration curve suitable for the biosensor 2, the computation unit 18 selects the proper calibration curve and performs the intended computation by applying the measurement result obtained by the current measurer 14 to the calibration curve.

The controller 19 controls the operation of each of the above-described parts Vcc and 14-18 to make these parts perform the analysis of the sample supplied to the biosensor 2. Further, the controller 19 handles error when the abnormality detector 16 detects an abnormality in each of the detection terminal pairs 11 and 12. The error-handling includes at least the process to withhold the computation of the blood glucose level, such as the process to withhold the operation of the information recognizer 17 or the computation unit 18, for example.

The detector 15, the abnormality detector 16, the information recognizer 17, the computation unit 18 and the controller 19 may be provided by a combination of a CPU, a ROM and a RAM, for example.

The blood glucose level measurement operation using the blood glucose level measurer 1 and the biosensor 2 will be described below. It is assumed that information for enabling selection of a calibration curve is applied to the recognition target portion 24 of the biosensor 2 and the information recognizer 17 of the blood glucose level measurer 1 recognizes the information as to the calibration curve.

The blood glucose level measurement is performed automatically at the blood glucose level measurer 1 by mounting the biosensor 2 to the blood glucose level measurer 1 and supplying blood to the biosensor 2.

First, in the blood glucose level measurer 1, the abnormality detector 16 determines whether or not there is an abnormality in the first and the second detection terminal pairs 11, 12. Specifically, individually with respect to each of the detection terminal pairs 11 and 12, the abnormality detector 16 checks whether or not the signal generated by the detector 15 shifts from a Low signal to a High signal in the process of mounting the biosensor 2 to the mount portion 10. When at least either of the signal generated based on the detection terminal pair 11 or the signal generated based on the detection terminal pair 12 does not shift from a Low signal to a High signal, the abnormality detector 16 determines that there is an abnormality in the detection terminal pairs 11, 12. When the abnormality detector 16 detects an abnormality of the first and the second detection terminal pairs 11, 12, the controller 19 performs the error-handling. For instance, the error-handling includes at least the process to withhold the computation of the blood glucose level (e.g. the process to withhold the operation of the information recognizer 17 or the computation unit 18) and the process to notify the existence of abnormality in the detection terminal pairs 11, 12. The abnormality can be notified by utilizing a display of the blood glucose level measurer 1 or by sound.

When the abnormality detector 16 confirms that the signal generated by the detector 15 is shifted from a Low signal to a High signal in the process of mounting the biosensor 2 to the mount portion 10, the abnormality detector determines that there is no abnormality in the detection terminal pairs 11, 12. Subsequently, the information recognizer 17 recognizes the information applied to the recognition target portion 24 of the biosensor 2. For instance, in the biosensor 2 shown in FIGS. 3-6, the through-hole 24a is formed only at the first detection target region 24A of the recognition target portion 24, so that the information recognizer 17 recognizes the Low/High signal combination. Therefore, the information recognizer 17 recognizes that the information applied to the recognition target portion 24 corresponds to the calibration curve number 2, as shown in FIG. 10.

When the biosensor 2 is mounted to the blood glucose level measurer 1, the ends 25b and 26b of the working electrode 25 and the counter electrode 26 of the biosensor are brought into contact with the measurement terminals 13A and 13B of the blood glucose level measurer 1. In the biosensor 2, the blood introduced into the capillary 23 through the introduction port 23A travels toward the exhaust port 22B due to the capillary phenomenon occurring in the capillary 23. As the blood travels, the reagent portion 28 is dissolved by the blood, and a liquid phase reaction system is established in the capillary 23. For instance, in the liquid phase reaction system, the oxidoreductase reacts specifically with glucose in blood to extract an electron from glucose, and the electron is supplied to the electron mediator, whereby the electron mediator becomes the reduced form.

In the blood glucose level measurer 1, when the abnormality detector 16 determines that there is no abnormality in the detection terminal pairs 11, 12, a voltage is applied to the liquid phase reaction system by utilizing the working electrode 25 and the counter electrode 26. As a result, electrons are supplied from the electron mediator in the reduced form to the working electrode 25. The amount of electrons supplied to the working electrode 25 is measured as the response current by the current measurer 14 of the blood glucose level measurer 1. In the computation unit 18, the blood glucose level is computed based on the response current measured by the current measurer 14 and the calibration curve recognized by the information recognizer 17. Specifically, in the computation unit 18, the blood glucose level is computed by applying e.g. the response current, which is measured when a predetermined time period has lapsed from the supply of blood to the capillary 23, to the calibration curve.

In blood glucose level measurer 1, the abnormality detector 16 detects an abnormality of the detection terminal pairs 11, 12 before the information recognizer 17 recognizes the information applied to the recognition target portion 24 of the biosensor 2 and before the computation unit 18 computes the blood glucose level. Further, when the abnormality detector 16 detects an abnormality of the detection terminal pairs 11, 12, the controller 19 performs control to withhold the computation of the blood glucose level. Therefore, in the blood glucose level measurer 1, it is possible to avoid such a situation that the blood glucose level is measured in spite of the existence of an abnormality in the detection terminal pairs 11, 12. As a result, measurement errors due to the abnormality of the detection terminal pairs 11, 12 can be avoided, and the measurement reliability can be enhanced.

In this embodiment, each of the detection terminal pairs shifts from the contact state to the non-contact state in the process of mounting the biosensor to the mount portion. However, contrary to this, the detection terminal pairs may shift from the non-contact state to the contact state in the process of mounting the biosensor to the mount portion. In this case, the abnormality detector determines that each of the detection terminal pairs is in the normal condition when the shift from a High signal to a Low signal is confirmed and otherwise determines that there is an abnormality.

The present invention is not limited to an analyzer which uses a biosensor designed to measure the glucose level in blood by an electrochemical technique, and is also applicable to an analyzer for other analytical tools. For instance, the present invention is applicable to an analyzer for measuring a component in blood other than glucose (e.g. lactic acid or cholesterol), an analyzer for performing analysis by using a sample other than blood or an analyzer for analyzing a particular component (e.g. glucose, lactic acid or cholesterol) contained in a sample (e.g. blood or urine) by an optical technique.

The invention claimed is:

1. An analyzer to be used with an analytical tool mounted thereto and used for analyzing a particular component contained in a sample supplied to the analytical tool, the analyzer comprising:
   at least one detection terminal pair including a first detection terminal and a second detection terminal which are capable of selecting a mutually contacting state and a non-contacting state;
   a current measurer operably connected to the at least one detection terminal pair and configured to measure in a process of mounting the analytical tool whether current flows between the first detection terminal and the second detection terminal;
   a detector operably connected to the current measurer and configured to:
      detect a state of contact of the first detection terminal and the second detection terminal based on measurements by said current measurer in the process of mounting the analytical tool,
      determine a current flow between the first detection terminal and the second detection terminal based on measurements by said current measurer,
      generate a first signal if the current flow is smaller than a predetermined threshold, and
      generate a second signal if the current flow is greater than the predetermined threshold; and
   an abnormality detector operably connected to the detector and configured to detect an abnormality of said at least one detection terminal pair based on either the first signal or the second signal as generated by said detector,
   wherein the abnormality detector determines, in the process of mounting the analytical tool, that there is no abnormality in the detection terminal pair when shifting of the first and the second detection terminals from a mutually contacting state to a non-contacting state is confirmed and determines that there is an abnormality in the detection terminal pair when shifting of the first and the second detection terminals from the mutually contacting state to the non-contacting state is not confirmed.

2. The analyzer according to claim 1, wherein, in normal conditions, the first and the second detection terminals are in contact with each other when the analytical tool is not mounted and separate from each other in a process of mounting the analytical tool.

3. The analyzer according to claim 2, wherein the detector is configured to detect a state of contact of the first detection terminal and the second detection terminal after converting, an analog electrical signal obtained by utilizing the first and the second detection terminals into a digital electrical signal; and wherein the abnormality detector is configured to determine that there is no abnormality in the detection terminal pair when a level of the digital electrical signal is higher than the predetermined threshold and determines that there is an abnormality in the detection terminal pair when the level of the digital electrical signal is lower than the predetermined threshold.

4. The analyzer according to claim 1, wherein at least one of the first and the second detection terminals is in a form of a leaf spring.

5. The analyzer according to claim 1, wherein the analytical tool to be used is provided with a recognition target portion which includes at least one predetermined detection target region and to which intended information is applied by selecting whether or not a through-hole is to be formed at the detection target region; wherein the first and the second detection terminals are located at a position corresponding to the detection target region when the analytical tool is mounted and utilized for recognizing information applied to the recognition target portion.

6. The analyzer according to claim 5, wherein information as to the analytical tool is applied to the recognition target portion of the analytical tool to be used.

7. The analyzer according to claim 1 wherein the analytical tool to be used is an electrochemical sensor.

8. The analyzer according to claim 1, wherein the analytical tool to be used is configured to analyze a particular component contained in blood.

9. The analyzer according to claim 1, further comprising a controller for withholding analysis of the particular component in the sample when the abnormality detector determines that there is an abnormality in the detection terminal pair.

\* \* \* \* \*

UNITED STATES PATENT AND TRADEMARK OFFICE
CERTIFICATE OF CORRECTION

| | |
|---|---|
| PATENT NO. | : 8,357,273 B2 |
| APPLICATION NO. | : 11/547945 |
| DATED | : January 22, 2013 |
| INVENTOR(S) | : Kawai |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1337 days.

Signed and Sealed this
Eleventh Day of November, 2014

Michelle K. Lee
*Deputy Director of the United States Patent and Trademark Office*